United States Patent [19]
Crimmin et al.

[11] Patent Number: 5,300,674
[45] Date of Patent: Apr. 5, 1994

[54] P2′-MODIFIED HYDROXAMIC ACID COLLAGENASE INHIBITORS

[75] Inventors: M. J. Crimmin, Marlow Bottom; A. H. Davidson, Witney; R. P. Beckett, Aston, all of England

[73] Assignee: British Bio-Technology Limited, Oxford, England

[21] Appl. No.: 760,741

[22] Filed: Sep. 16, 1991

[30] Foreign Application Priority Data

Feb. 7, 1991 [GB] United Kingdom ................. 9102635

[51] Int. Cl.$^5$ .................. C07C 229/34; C07C 259/06
[52] U.S. Cl. ...................................... 560/42; 562/451; 562/623
[58] Field of Search ............... 562/621, 444, 455, 451, 562/623; 514/575, 563; 560/42

[56] References Cited

U.S. PATENT DOCUMENTS

| | | | |
|---|---|---|---|
| 4,105,789 | 8/1978 | Ondetti et al. | 560/153 X |
| 4,496,540 | 1/1985 | Kim | 514/19 |
| 4,599,361 | 7/1986 | Dickens et al. | 514/575 |

FOREIGN PATENT DOCUMENTS

| | | |
|---|---|---|
| 0012401A1 | 6/1980 | European Pat. Off. |
| WO90/05716 | 5/1990 | PCT Int'l Appl. |
| WO90/05719 | 5/1990 | PCT Int'l Appl. |

OTHER PUBLICATIONS

Woolley et al., Arthritis and Rheumatism 20 pp. 1231-1239 (1977).
Evans, et al., J. Am. Chem. Soc. 104: pp. 1737-1739 (1982).
Cawston and Barrett, Anal. Biochem. 99: pp. 340-345 (1979).
Cawston and Murphy, Methods in Enzymology 80: pp. 711-722 (1981).

*Primary Examiner*—Joseph Paul Brust
*Attorney, Agent, or Firm*—Allegretti & Witcoff, Ltd.

[57] ABSTRACT

Compounds of general formula I:

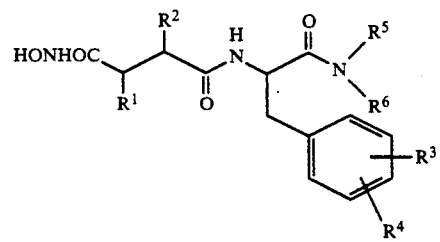

Wherein:
$R^1$, $R^2$, $R^3$, $R^4$, $R^5$, and $R^6$ are variables.

These compounds have collagenase inhibition activity and are useful in the management of disease involving collagen degradation. Its uses include rheumatoide arthritis, corneal ulceration, osteoporosis, periodontitis, gingivitis and tumour invasion.

6 Claims, No Drawings

P2'-MODIFIED HYDROXAMIC ACID COLLAGENASE INHIBITORS

A number of small peptide like compounds which inhibit metalloproteinase have been described. Perhaps the most notable of these are those relating to the angiotensin converting enzyme (ACE) where such agents act to blockade the conversion of the decapeptide angiotensin I to angiotensin II, a potent pressor substance. Compounds of this type are described in EP-A-0012401.

Certain hydroxamic acids have been suggested as collagenase inhibitor as in U.S. Pat. No. 4 599 361, WO-A-9005716 and WO-A-9005719. other hydroxamic acids have been prepared as ACE inhibitors, for example, in U.S. Pat. No. 4,105,789, while still others have been described as enkephalinase inhibitors as in U.S. Pat. No. 4,495,540.

The hydroxamic acids of the current invention act as inhibitors of mammalian collagenase which initiates collagen breakdown. There is evidence implicating collagenase as one of the key enzymes in the breakdown of articular cartilage and bone in rheumatoid arthritis (*Arthritis and Rheumatism*, 20, 1131-1239, (1977)). Potent inhibitors of collagenase are useful in the treatment of rheumatoid arthritis and related diseases in which collagenolytic activity is important. These diseases include corneal ulceration, osteoporosis, periodontitis, gingivitis and tumour invasion.

The current invention relates to a series of hydboxamic acids, of formula I, which act as inhibitors of metalloproteinase, their preparation, pharmaceutical compositions containing them, and the intermediates involved in their preparation.

Wherein:

$R^1$ is hydrogen, $C_1-C_6$ alkyl, phenyl, substituted phenyl, phenyl($C_1-C_6$ alkyl), or heterocyclyl; or $R^1$ is $ASO_nR^7$ wherein A represents a $C_1-C_6$ hydrocarbon chain, optionally substituted with one or more $C_1-C_6$ alkyl, phenyl or substituted phenyl groups n=0,1,2;

$R^7$ is $C_1-C_6$ alkyl, phenyl, substituted phenyl, phenyl ($C_1-C_6$ alkyl), heterocyclyl, ($C_1-C_6$ alkyl)acyl, thienyl or phenacyl;

$R^2$ is hydrogen, $C_1-C_6$ alkyl, $C_2-C_6$ alkenyl, phenyl ($C_1-C_6$alkyl) or cycloalkyl($C_1-C_6$ alkyl);

$R^3$ and $R^4$ are selected from hydrogen, halogen, cyano amino, amino ($C_1-C_6$) alkyl, amino di($C_1-C_6$) alkyl, amino($C_1-C_6$)alkylacyl, aminophenacyl, amino (substituted) phenacyl, amino acid or derivative thereof, hydroxy, oxy($C_1-C_6$)alkyl, oxyacyl, formyl, carboxylic acid, carboxamide, carboxy($C_1-C_6$) alkylamide, carboxyphenylamide, carboxy($C_1-C_6$) alkyl, hydroxy($C_1-C_6$)alkyl, ($C_1-C_6$)alkyloxy($C_1-C_6$) alkyl or acyloxy($C_1-C_6$)alkyl, ($C_1-C_6$)alkylcarboxylic acid, or ($C_1-C_6$) alkylcarboxy($C_1-C_6$) alkyl; or $R^3$ is $OCH_2COR^8$ and $R^4$ is hydrogen;

wherein $R^8$ is hydroxyl, $C_1-C_6$ oxyalkyl, $C_1-C_6$ oxyalkylphenyl, amino, $C_1-C_6$ aminoalkyl, $C_1-C_6$ aminodialkyl, $C_1-C_6$ aminoalkylphenyl, an amino acid or derivative thereof; or $R^3$ is $OCH_2CH_2OR^9$ and $R^4$ is hydrogen;

wherein $R^9$ is $C_1-C_6$ alkyl, $C_1-C_6$ alkylphenyl, phenyl, substituted phenyl, ($C_1-C_6$ alkyl)acyl, or phenacyl; or $R^3$ is $OCH_2CN$ and $R^4$ is hydrogen;

$R^5$ is hydrogen or $C_1-C_6$ alkyl, or ($C_1-C_6$) alkylphenyl;

$R^6$ is hydrogen or methyl; or a salt thereof;

specifically excluded are compounds wherein:

$R^3=R^4$ hydrogen or $R^3=R^4=$hydroxy or $R^3$ hydrogen and $R^4=$oxybenzyl or $R^3$ hydrogen and $R^4=$oxy($C_1-C_6$ alkyl).

Hereafter in this specification the term "compound" includes salt unless the context requires otherwise.

As used herein the term "$C_1-C_6$ alky" refers to a straight or branched chain alkyl moiety having from one to six carbon atoms, including for example, methyl, ethyl, propyl, isopropyl, butyl, t-butyl, pentyl, hexyl and the like.

The term "$C_2-C_6$ alkeny" refers to a straight or branched chain alkyl moiety having two to six carbons and having in addition one double bond, of either E or Z stereochemistry where applicable. This term would include, for example, vinyl, 1-propenyl, 1- and 2-butenyl, 2-methyl-2-propenyl etc.

The term "cycloalkyl" refers to a saturated alicyclic moiety having from 3 to 8 carbon atoms and includes for example, cyclopropyl, cyclobutyl, cyclopentyl, cyclohexyl and the like.

The term 'heterocyclyl' refers to a saturated or unsaturated ring containing at least one hetero atom such as nitrogen, oxygen or sulphur and includes for example, furan, pyrrole, thiophene, morpholine, pyridine, dioxane, imidazoline, pyrimidine and pyridazine.

The term "substituted", as applied to a phenyl or other aromatic ring, means substituted with up to four substituents each of which independently may be $C_1-C_6$ alkyl, $C_1-C_6$ alkoxy, hydroxy, thiol, $C_1-C_6$ alkylthiol, amino, halo (including fluoro, chloro, bromo and iodo), trifluoromethyl, nitro, —COOH, —COONH$_2$ or —CONHR$^A$ wherein R$^A$ represents a $C_1-C_6$ alkyl group or the characteristic side chain of an amino acid such as alanine, valine, leucine, isoleucins, phenylalanine, tryptophan, methionine, glycine, serine, threonine, cysteine, tyrosine, asparagine, glutamine, aspartic acid, glutamic acid, lysine, arginine or histidine.

The term "amino acid" means one of the following R or S amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

Derivatives of amino acids include acid halides, esters and substituted or unsubstituted amides, for example N methyl amide.

There are several chiral centres in the compounds according to the invention because of the presence of asymmetric carbon atoms.

The presence of several asymmetric carbon atoms gives rise to a number of diastereomers with the appropriate R or S stereochemistry at each chiral centre. The invention is understood to include all such diastereomers and mixtures thereof.

Preferred compounds include those in which, independently or in combination:

$R^1$ represents a hydrogen atom or a $C_1-C_4$ alkyl, or phenyl group; or $R^1$ represents $ASO_nR^7$ in which A is $C_1-C_4$ hydrocarbon chain alkyl (for example methylene), $n=0$, and $R^7$ is a phenyl, substituted phenyl or thienyl group;

$R^2$ represents a $C_1-C_5$ alkyl (for example isobutyl) group;

$R^3$ represents cyano, aminoalkylacyl or $OCH_2COR^8$ and $R^4$ is hydrogen;

Wherein $R^8$ represents a hydroxyl group, $C_1-C_6$ oxyalkyl, amino, $C_1-C_6$ aminoalkylphenyl, $C_1-C_6$ aminodialkyl, or an amino acid or derivative thereof;

$R^5$ represents a $C_1-C_4$ alkyl (for example methyl) group;

$R^6$ represents a hydrogen atom.

Particularly preferred compounds include:

(4-(N-Hydroxyamino)-2R-isobutylsuccinyl]-L-(4-oxymethylcarboxlic acid) phenylalanine-N-methylamide;

[4-(N-Hydroxyamino)-2R-isobutylsuccinyl]-L-(4-oxymethylcarboxy-N-methylamide) phenylalanine-N-methylamide;

[4-(N-Hydroxyamino)-2R-isobutylsuccinyl]-L-(4-oxymethylcarboxy-beta-alanine) phenylalanine-N-methylamide;

(4-(N-Hydroxyamino)-2R-isobutylsuccinyl]-L-(4-(oxymethylcarboxy-glycine)phenylalanine-N-methylamide;

[4-(N-Hydroxyamino)-2R-isobutylsuccinyl]-L-(4-oxymethylcarboxy-N-benzylamide) phenylaianine-N-methylamide;

[4-(N-Hydroxyamino)-2R-isobutylsuccinyl]-L-(4-cyano) phenylalanine-N-methylamide;

[4-(N-Hydroxyamino)-2R-isobutylsuccinyl]-L-(4-acetamido) phenylalanine-N-methylamide.

Compounds of the general formula I may be prepared by any suitable method known in the art and/or by the following process, which itself forms part of the invention.

According to a second aspect of the invention, there is provided a process for preparing a compound of general formula I as defined above, the process comprising:

(a) deprotecting (for example by hydrogenation) a compound of general formula II

II

Wherein:

$R^1$, $R^2$, $R^3$, $R^4$, $R^5$ and $R^6$ are as defined in the general formula I and Z represents a suitable protective group (e.g. tert-butyl, tertbutylsily, benzyl or substituted benzyl);

(b) reacting a compound of general formula III

III

Wherein:

$R^1$, $R^2$, $R^3$, $R^4$, $R^5$, and $R^6$ are as defined in the general formula I, with hydroxylamine or a salt thereof; and (c) optionally after step (a) or step (b) converting a compound of general formula I into another compound of general formula I.

Compounds of general formula I which are sulphoxide or sulphones can be derived from thio compounds of general formula I by oxidation. Alternatively, compounds of general formula II, or III which contain sulphur can be oxidised.

A compound of general formula II can be obtained by coupling, for example by conventional coupling techniques, a compound of general formula III with an O-protected hydroxylamine of formula $NH_2OZ$; wherein Z is as defined in general formula II.

A compound of general formula III can be prepared by (a) de-esterifying (for example under acid or base catalysis) a compound of general formula IV

IV

Wherein:

$R^1$, $R^2$, $R^3$, $R^4$, $R^5$, and $R^6$ are as defined in the general formula I, and $R^{10}$ represents a $C_1-C_6$ alkyl or benzyl group; or (b) by reacting a compound of general formula V

V

Wherein:

$R^2$, $R^3$, $R^4$, $R^5$, and $R^6$ are as defined in the general formula I, either with a thiol of general formula $R^7SH$, wherein $R^7$ is as defined in general formula I, to give a compound of general formula III in which $R^1$ is $ASO_nR^7$, A represents a methylene group and n is 0.

or with compound $R^1X$ where $R^1$ is benzyl or substituted benzyl and X is F, Cl, Br of I in the presence of a palladium catalyst to provide a compound of general formula VI

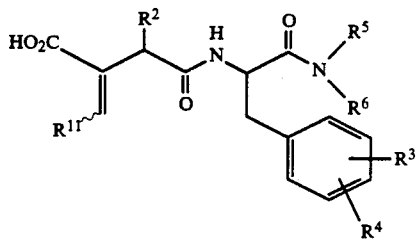     VI

Wherein:
$R^2$, $R^3$, $R^4$, $R^5$, and $R^6$ are as defined in the general formula I, and $R^1$ is benzyl or substituted benzyl, which may be converted to a compound of general formula III wherein $R^2$ is benzyl or substituted benzyl, by hydrogenation; or (c) by converting a compound of general formula III into another compound of general formula III.

A compound of general formula V can be prepared from a compound of general formula IV

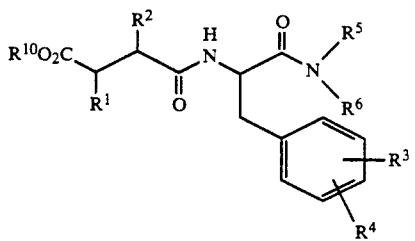     IV

Wherein:
$R^2$, $R^3$, $R^4$, $R^5$, and $R^6$ are as defined in the general formula I, $R^1$ is carboxybenzyl or carboxy ($C_1$-$C_6$) alkyl and R10 is benzyl or ($C_1$-$C_6$) alkyl, and $R^{10}$ is benzyl or ($C_1$-$C_6$) alkyl, by de-esterification (for example by hydrogenation) followed by reaction with formaldehyde in the presence of morpholine.

A compound of general formula IV can be prepared (a) By reacting, for example by conventional coupling techniques, an acid of formula VII, or an activated ester derivative thereof,

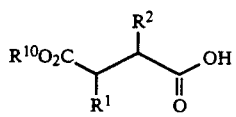     VII

Wherein:
$R^1$ and $R^2$ are as defined in the formula I, and $R^{10}$ is as defined above.

with an amine of general formula VIII

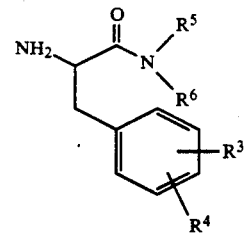     VIII

Wherein:
$R^3$, $R^4$, $R^5$, and $R^6$ are as defined in the general formula I;

(b) by converting a compound of general formula IV into another compound of general formula IV.

An amine of general formula VIII can be prepared by deprotection (for example with trifluoroacetic acid) of a compound of general formula IX

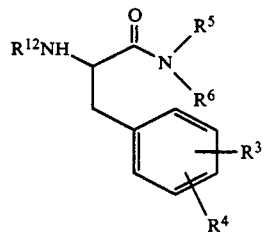     IX

Wherein:
$R^{12}$ is a conventional amine protecting group and $R^3$ $R^4$, $R^5$ and $R^6$ are as defined in general formula I.

A compound of general formula IX may be prepared by coupling an acid of general formula X

     X

Wherein:
$R^3$ and $R^4$, are defined as in general formula I, with an amine of general formula XI $$HN\begin{matrix}R^5\\R^6\end{matrix}$$     XI Wherein:
$R^5$ and $R^6$ are as defined in general formula I A compound of general formula X may be prepared (a) by-reaction of an aryl halide of general formula XII

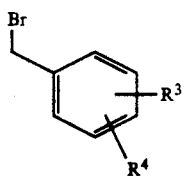

Wherein $R^3$ and $R^4$ are as defined in general formula I with a glycinate anion equivalent of formula XIII

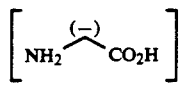

followed by acid hydrolysis, protection of the amino function and base catalysed release of the carboxylic acid; or (b) by converting a compound of general formula X to another compound of general formula X.

A compound of general formula VII may be prepared by reaction of a compound of general formula XIV

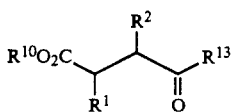

Wherein:
$R^2$ is as defined in the general formula I, $R^1$ is hydrogen, $R^{10}$ is as described above and $R^{13}$ is a chiral auxillary for example as described by Evans (*J. Amer. Chem. Soc.*, 104, 1737, (1982)).
with lithium hydroxide/hydrogen peroxide.

A compound of general formula XIV may be produced by alkylation of the anion of a compound of general formula XV

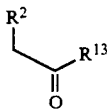

Wherein:
$R^2$ is as defined in the general formula I and $R^{13}$ is a chiral auxillary,
with an alkylating agent of general formula XVI.

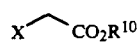

Wherein:
$R^{10}$ is as described above and X is a leaving group, for example bromide, iodide or triflate.

Compounds of general formulae XI, XII, XIII, XV and XVI and other reagents are either available commercially or can be synthesised by simple chemical procedures.

The potency of compounds of the present invention to act as inhibitors of collagenase was determined by the procedure of Cawston and Barrett, (Anal. Biochem., 99, 340–345, 1979) whereby a 1 mm solution of the inhibitor being tested or dilutions thereof is incubated at 37° C. for 16 hours with collagen and collagenase (buffered with Tris HCl - $CaCl_2$; pH 7.6). The collagen is acetylated $^{14}C$ collagen prepared by the method of Cawston and Murphy (*Methods in Enzymolocly*, 80, 711, (1981)). The samples are centrifuged to sediment undigested collagen and an aliquot of the radioactive supernatant removed for assay on scintillation counter as a measure of hydrolysis. The collagenase activity in the presence of 1 mM inhibitor, or a dilution thereof, is compared to activity in a control devoid of inhibitor and the results reported as that inhibitor concentration effecting 50% inhibition of the collagenase.

In a further aspect of the invention there is provided the use of a compund of general formula I in medicine, particularly in a method of treatment of diseases in which collagenolytic activity is important.

In another aspect of the invention there is provided the use of a compound of general formula I in the preparation of an agent for the treatment of diseases in which collagenolytic activity is important.

The invention also provides a pharmaceutical composition comprising one or more compounds of general formula I in association with one or more non-toxic pharmaceutically acceptable carriers and/or diluents and/or adjuvants. Other active ingredients may also be included in the compositions of the invention.

The compositions of the present invention may be formulated for administration by any route depending on the disease being treated. The compositions may be in the form of tablets, capsules, powders, granules, lozenges, liquid or gel preparations, such as oral, topical, or sterile parental solutions or suspensions.

Tablets and capsules for oral administration may be in 1.2 unit dose presentation form, and may contain conventional excipients. Examples of these are binding agents such as syrup, acacia, golatin, sorbitol, tragacanth, and polyvinylpyrollidone; fillers for example lactose, sugar, maize-starch, calcium phosphate, sorbitol or glycine; tabletting lubricants, for example magnesium sterate, talc, polyethylene glycol or silica,, disintegrants, for example potato starch, or acceptable wetting agents such as sodium lauryl sulphate. The tablets may be coated according to methods well known in normal pharmaceutical practice. oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup,gelatin, hydrogenated edible fats; emulsifiying agents, for example lecithin, sorbitan monooleate, or acacia; non-aqueous vehicles (which may include edible oils) for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg. A suitable daily dose for a mammal amy vary widely depending on the condition of the patient. However, a dose of about 0.1 to 300 mg/kg body weight, particularly from about 1 to 100 mg/kg body weight may be appropriate.

For topical application to the skin the drug may be made up into a cream, lotion or ointment. Cream or ointment formulations that may be used for the drug are conventional formulations well known in the art, for example, as described in standard text books of pharmaceutics such as the British Pharmacopoeia.

For topical applications to the eye, the drug may be made up into a solution or suspension in a suitable sterile aqueous or non-aqueous vehicle. Additives, for instance buffers such as sodium metabisulphite or disodium edeate; preservatives including bactericidal and fungicidal agents, such as phenyl mercuric acetate or nitrate, benzalkonium chloride or chlorohexidine, and thickening agents such as hypromellose may also be included.

The dosage employed for the topical administration will, of course, depend on the size of the areak being treated. For the eyes each dose will be typically in the range from 10 to 100 mg of the drug.

The active ingredient may also be administered parenterally in a sterile medium. The drug depending on the vehicle and concentration used, can either be suspended or dissolved in the vehicle. Advantageously, adjuvants such as local anaesthetic, preservatives and buffering agents can be dissolved in the vehicle.

For use in the treatment of rheumatoid arthritis the compounds of this invention can be administered by the oral route or by injection intra-articularly into the affected joint. The daily dosage for a 70 kg mammal will be in the range of 10 mgs to 1 gram.

The following examples illustrate the invention, but are not intended to limit the scope in any way.

The following abbreviations have been used in the Examples:

DCM—Dichloromethane
DMF—N,N-Dimethylformamide
HOBT—Hydroxybenztriazole
NMM—N-Methylmorpholine
TFA—Trifluoroacetic acid
THF—Tetrahydrofuran
WSCDI—N-(Dimethylaminoethyl)-N'-ethylcarbodiimide.

EXAMPLES

Example 1

4-(N-Hydroxyamino)-2R-isobutylsuccinyl]-L-(4-oxymethylcarboxylic acid)-phenylalanine-N-methylamide

Example 1a

N-(4-Methyl2entanoyl)-4S-phenylmethyl-2-oxazolidinone

A dry 500 ml flask equipped with a magnetic stirrer was charged with (S)-4-Phenylmethyl-2-oxazolidinone (17.72 g, 0.1 mol), this was capped with a rubber septum and flushed with $N_2$. Anhydrous THF (300 ml) was added via cannula and the resulting solution was cooled to −78° C. in an acetone/dry ice bath. A solution of 1.47M n-butyllithium in hexane (68.4 ml, 0.101 mol) was transferred via cannula to a dry, septum-stoppered 100 ml dropping funnel. This was added dropwise to the THF solution over 10 minutes.

4-methyl valeric acid chloride (14.80 g 0.11 mol) was added in one portion by syringe after completion of the addition of n-butyllithium. The resulting solution was stirred at −78° C. for 30 minutes and then allowed to warm to ambient temperature over 30 minutes. Excess of the acid chloride was quenched by the addition of aq. $NH_4Cl$ (60 ml) and the bulk of the solvent was removed. The resulting slurry was extracted with dichloromethane (2×80 ml). The combined organic extracts were washed with 1M NAOH (75 ml) brine (75 ml) dried X( $Na_2SO_4$ anhyd.) and filtered. The solvent was removed to yield a yellow oil (29.20 g, 106%).

Analysis calculated for $C_{16}H_{21}NO_3$ MWt=275.34 delta$_H$ (250 MHz, $CDCl_3$), 0.97 (6H, d, $C(CH_3)_2$, J=6.2 Hz), 1.53–1.76 (3H, m, $CH_2CHMe_2$), 2.78 (1H, dd, $CH_2Ph$, J=9.5 Hz), 2.85–3.05 (2H, m, $COCH_2$) 3.30 (1H, dd, $CH_2Ph$, J=3.3 Hz) 4.16–4.25 (2H, m, $CH_2OCO$) 4.63–4.73 (1H, m, CHBnz) 7.19–7.34 (5H, m, $C_6H_5$)

Example 1b

N(4-(t-Butoxy)-2R-isobutylsuccinyl)-4S-phenylmethyl-2-oxazolidinone

N-(4-Methylpentanoyl)-4S-phenylmethyl-2-oxazolidinone (20 g, 0.0726 mol) was placed in a dry 1 litre 3-necked flask to which was added dry THF (400 ml). The mixture was kept under a stream of Argon and cooled to −78° C. (dry ice/acetone). Sodium hexamethyldisilylamide (1M solution in THF, 0.0726 mol, 72.6 ml) was added dropwise through a dropping funnel (it was added to the funnel via syringe). After stirring for 20 minutes, t-butylbromoacetate (21.02 g, 15.8 ml, 0.1089 mol, 1.5 equiv.) was added dropwise over 1 minute, to give an orange solution. The mixture was kept at −78° C. and allowed to warm to −50° C. over 2 hours (after which time it turned pink). The reaction was then quenched by adding acetic acid (10.90q, 10.4 ml, 0.1815 mol, 2.5 equiv.) in ether (50 ml) at −50° C. whereupon the solution became colourless. The solvent was removed and the resulting slurry partitioned between ethyl acetate and brine. The ethyl acetate layer was washed once with brine and the original brine layer was back-extracted with ethyl acetate. The combined organic layers were dried and the solvent removed, giving a yellow oil which crystallised on cooling overnight to yield the title compound as a crystalline solid (21.36 g, 76%).

Analysis calculated for $C_{22}H_{31}O_5N$ MWt=389.48 delta$_H$ (250 MHz, $CDCl_3$) 0.91–0.96 (6H, dd, $CMe_2$, J=4.5 Hz), 1.44 (9H, s, $CMe_3$) 1.24–1.72 (3H, m, $CH_2CHMe_2$), 2.49 (1H, dd, CH Ph, J=4.6 Hz), 2.72 (1H, dd, $CH_2CO_2CH(CH_3)_31$ J=2.3 Hz), 3.36 (1H, dd, $CH_2Ph$, J−3.25 Hz), 4.16–4.18 (2H, m, CH2OCO), 4.20–4.35 (1H, m, CH—CO), 4.62–4.72 (1H, m, CHBz,), 7.24–7.38 (5H, m, $C_6H_5$)

[alpha]$^{25}$D=+66.9 (c=1, MeOH)

Example 1c 4-(t-Butoxy)-2R-isobutylsuccinic acid

N(4-(t-Butoxy)-2R-isobutylsuccinyl)-4S-phenylmethyl-2-oxazolidinone (15.30 g, 0.039 mol) was placed in a 1 litre flask with a stirrer bar and to it was added 750 ml of 4.1 THF:$H_2O$. This solution was stirred and cooled to 0° C. (ice/acetone bath) then 60% aq. $H_2O_2$ (4.5 ml, 0.157 mol, 4 equiv) was added via syringe over 5 mins, 1.2 followed by Li(OH)$_2$ (2.65 g, 0.063 mol, 1.6 equiv.) in 100 ml water. The reaction mixture was stirred for 1h at 0° C. TLC (10% methanol/dichloromethane) showed complete reaction (product gave a yellow spot on TLC on staining with bromocresol green and heating). The reaction mixture was quenched with $NANO_2$ (10.88 g, 0.157 mol, 4 equiv.), the final pH was 12–13. THF was removed in-vacuo and the aqueous layer extracted with dichloromethane (3×200 ml) to recover the chiral auxliary. The organic extracts were dried ($MgSO_4$ anhyd.), solvent removed in-vacuo and the resulting solid chiral auxiliary (7.05 g, 0.039 mol, 100%) recrystallised from ethyl acetate/hexane (2:1)

[alpha]$^{25}$D = 13.00 (x = 1, MeOH)

[alpha]$^{25}$D 4.9° (c = 1, EtOH)

The aqueous layer was cooled in an ice bath and acidified to pH 5–6 with 2M HCl. The resulting cloudy solution was extracted with ethyl acetate (4×200 ml), readjusting the pH to 5–6 in between extractions. The combined organic extracts were dried over MgSO$_4$, filtered and the solvent was removed to yield the title compound as a pale yellow oil (8.21 g, 91%).

delta$_H$ (250 MHz, CDCl$_3$) 0.93 (6H, dd, J=7, 8 Hz), 1.28 (1H, m), 1.64 (1H, m), 2.38 (1H, dd, J=16, 5 Hz), 2.59 (1H, dd, J=16, 9 Hz), 2.85 (1H, m).

[alpha]$^{25}$D = +10.4 (c = 1, MeOH)

Example 1d

Pentafluorophenyl 4-(t-butoxy)-2R-isobutylsuccinate

A solution of the chiral acid (from example 1c, 5.0 g, 21.7 mmol) and pentafluorophenol (8.0 g, 43 mmol) in dichloromethane (50 ml) was cooled to 0° C. before dropwise addition of N-methylmorpholine (2.7 g, 26.7 mmol) followed by water-soluble carbodiimide (5.5 g, 28.7 mmol) in several portions. After the WSCDI had dissolved, a small amount of white insoluble material remained which did not dissolve on addition of N,N-dimethylformamide (5 ml). The mixture was allowed to warm to room temperature and was then stirred overnight at room temperature.

Solvents were removed on a rotary evaporator and the residue was resuspended in dichloromethane (100 ml) and washed successively with 1M HCl (2×200 ml), 0.5M Na$_2$CO$_3$ (2×200 ml) and brine (200 ml) and dried (Na$_2$SO$_4$)- TLC (CH$_2$Cl$_2$) showed a single UV-active spot (R$_f$ca.0.8) with a small amount of brown baseline impurity. The solution was therefore evaporated to a brown oil and flushed through a silica column (2×20 cm) with dichloromethane. UV-positive fractions were pooled and evaporated to give the pentafluorophenol ester as a pale yellow oil (8.31 g, 97%).

$C_{18}H_{21}F_5O_4$ MWt = 396.35 i.r. (neat) 1785, 1732 cm$^{-1}$ delta$_H$ (250 MHz, CDCl$_3$) 3.23 (1H, m), 2.74, 2.52 (2H, ddd, J=9.3, 5.2, 16.8 Hz), 1.75 (2H, m), 1.46 (10H, s and m), 0.98, 0.96 (6H, 2d, J=6.6 Hz)

delta$_C$ (250 MHz, CDCl$_3$) 171.3, 170.3, 143.2–138.9, 81.4, 41.0, 39.5, 37.7, 28.0, 25.8, 22.6, 22.1

Example 1e

O-Benzyl-L-tyrosine N-methylamide

N-Boc-O-benzyl tyrosine methylamide (5.29 g, 13.8 mmol) was taken up in CH$_2$Cl$_2$ (100 ml). To the solution at 0° C. TFA (10 ml) was added dropwise and the solution allowed to warm to ambient temperature. After 4 hours the solvent and TFA were removed under vacuum. Any remaining TFA was quenched with saturated NaHCO$_3$ solution (100 ml). The reaction mixture was extracted using CH$_2$Cl$_2$ (100 ml) and washed with saturated NaHCO$_3$ solution (100 ml) and brine (100 ml). The CH$_2$Cl$_2$ layer was dried over Na$_2$SO$_4$ and the solvent was removed under vacuum to give a white solid, which was recrystallised from ethyl acetate/hexane to yield the title compound as a white crystalline solid (3.35 g, 85.4%).

delta$_H$ (250 MHz, CDCl$_3$) 7.45–7.33 (5H, bm, Bn-H), 7.23 (1H, bs, CONHMe), 7.13 (2H, d, J=8.5 Hz, Ar-H), 6.93 (2H, d, J=8.6 Hz, Ar-H), 5.06 (2H, s, CH$_2$), 3.56 (1H, dd, J=5.1, 4.0 Hz, CH), 3.20 (1H, dd, J=9.8, 4.0 Hz, H of CH$_2$), 2.82 (3H, d, J=5.0 Hz, NHCH$_3$), 2.65 (1H, dd, J=9.3, 4.5 Hz, H of CH$_2$), 1.35 (2H, bs, NH$_2$).

Example 1f

[4-(t-Butoxy)-2R-isobutylsuccinyl]-L-(4-benzyloxy) phenylalanine-N-methylamide

To a stirred solution of the O-benzyl-L-tyrosine-N-methylamide (from example 1e, 3 g, 10.6 mmol) in DMF (100 ml) was added the chiral pentafluorophenyl ester (from example 1d, 8.37 g, 21.1 mmol) .The resulting solution was stirred at room temperature overnight. The DMF was removed under vacuum. The residue was taken up in CH$_2$Cl$_2$ (200 ml) and washed with saturated NAHCO$_3$ (2×100 ml), citric acid (2×100 ml) and brine (100 ml). The organic layer was dried over MGSO$_4$ and the solvent removed under vacuum to give a clear oil. Flash chromatography (flash silica, CH$_2$Cl$_2$ to 54 MeOH/CH2Cl2) gave the title compound as a pale yellow sdlid (4.95 g, 94%).

$C_{29}H_{40}N_2O_5$MWt = 496.65 delta$_H$(250 MHz, CDCl$_3$) 7.45–7.31 (5H, m, CH-21 to 25), 7.15 (2H, d, J=8.6 Hz, CH-9,11), 6.91 (2H, d, J=8.6 Hz, CH-8,12), 6.30 (1H, d, J=7.8 Hz, CONH), 5.92 (1H, m, CONHMe), 5.04 (2H, s, CH$_2$-19), 4.50 (1H, J=7.8 Hz, CH-5), 3.10 (1H, dd, J=6.3, 6.2 Hz, CH$_2$-6a), 2.82 (1H, dd, J=7.8 Hz, CH$_2$-6b), 2.70 (3H, d, J=4.8Hz, CH$_3$-13), 2.61 (1H, m, CH-3), 2.46 (2H, m, CH$_2$-2a, 2b), 1.52 (2H, m, 1.44, CH$_2$-15), (9H, s, CH$_3$-27, 28, 29), 1.19 (1H, m, CH-16), 0.88, 0.85 (6H, 2d, J=6.5, 6.3 Hz, CH$_3$-17, 18).

Example 1g

[4-(t-Butoxy)-2R-isobutylsuccinyl]-L-(4-hydroxy)-phenylalanine-N-methylamide

[4-(t-Butoxy)-2R-isobutylsuccinyl)-L-(4-benzyloxy) phenylalanine-N-methylamide (2.19 g, 4.4 mmol) was taken up in 10% cyclohexene/ethanol (30 ml) and 10% Pd/charcoal (0.219 g) added. The mixture was then heated under reflux. After 3 hours the hot solution was filtered through glass fibre paper and the black solid washed with methanol. The filtrate was concentrated under reduced pressure to give the title compound as a white foam (1.78 g, 99%).

$C_{22}H_{34}N_2O_5$ MWt = 405.6 delta$_H$ (250 MHz, CDCl$_3$) 7.08 (2H, d, J=8.6 Hz, CH-9, 11), 6.76 (2H, d, J=8.6 Hz, CH-8, 12), 6.35 (1H, d, J=8.0 Hz, CONH), 5.91 (1H, m, CONHMe), 4.50 (1H, q, J=7.9 HZ, CH-5), 3.06 (1H, dd, J=6.2 HZ, CH$_2$-6a), 2.96 (1H, dd, J=7.9 Hz, CH$_2$-6b), 2.71 (3H, d, J=4.8 Hz, CH$_3$-13), 2.61 (1H, m, CH-3),, 2.48 (2H, m, CH$_2$-2a, 2b), 1.52 (2H, m, CH$_2$-15), 1.44 (9H, s, CH$_3$-20, 21, 22), 1.25 (1H, m, CH-16), 0.86 (6H, d, J=6.4 Hz, CH$_3$-17, 18).

delta$_C$ (250 MHz, CDCl$_3$) 173.8, 170.4, 154.2, 128.8, 126.3, 114.2, 79.8, 76.1–75.1, 53.7, 39.6, 36.7, 36.1, 26.6, 24.8, 24.2, 21.21 20.9.

Example 1h

[4-(t-Butoxy)-2R-isobutylsuccinyl]-L-(4-oxymethylcarboxybenzyl)-phenylalanine-N-methylamide

[4-(t-Butoxy)-2R-isobutylsuccinyl]-L-(4-hydroxy) phenylalanine-N-methylamide (2.69 g, 6.6 mmol) was taken up in dry acetone (150 ml). Anhydrous Na$_2$CO$_3$ (0.84 g, 7.9 mmol) was added with stirring, followed by dropwise addition of benzyl-2-bromoacetate (2.27 g, 9.9 mmol). The reaction flask was flushed with argon and then the reaction mixture heated under reflux. After 48 hours the solvent was removed under vacuum. The residue was taken up in $CH_2Cl_2$ (100 ml) washed with saturated $Na_2CO_3$ (100 ml), 1M HCl (100 ml) and brine (100 ml), dried over $MGSO_4$ and the $CH_2Cl_2$ removed under vacuum to give a yellow oil. Flash chromatography (flash silica, 2% $MeOH/CH_2Cl_2$) gave the title compound as a white solid (1.91 g, 52%).

$C_{31}H_{42}N_2O_7$ Mwt=554.69

$delta_H$ (250 MHz, $CDCl_3$) 7.36 (5H, s, CH-23-27), 7.14 (2H, d, J=8.7 Hz, CH-9, 11), 6.83 (2H, d, J=8.7 Hz, CH-8, 12), 6.33 (1H, d, J=7.9 Hz, CONH), 5.92 (1H, m, CONHMe), 5.24 (2H, s, $CH_2$-21), 4.64 (2H, s, $CH_2$-19), 4.48 (1H, m, CH-5), 3.08 (1H, dd, J=6.2 Hz, $CH_2$-6a), 2.96 (1H, dd, J=7.9 Hz, $CH_2$-6b), 2.68 (3H, d, J=4.8 Hz, $CH_3$-13), 2.63 (1H, m, CH-3, 2.46 (2H, m, $CH_2$-2a,2b), 1.48 (2H, m, $CH_2$-15), 1.43 (9H, s, $CH_3$-29, 30, 31), 0.87, 0.84 (6H, 2d, J=6.5 Hz, $CH_3$-17,18).

Example 1i

[4-Hydroxy-2R-isobutylsuccinyl]-L-(4-oxymethtylcarboxybenzyl)-phenylalanine-N-methylamide

[4-(t-Butoxy)-2R-isobutylsuccinyl]-L-(4-oxymethylcarboxybenzyl)-phenylalanine-N-methylamide (2.12 g, 3.8 mmol) was taken up in 95% $TFA/H_2O$ (50 ml). The solution was stirred at 0° C. for 3 hours. $TFA/H_2O$ removed under vacuum. The residue was taken up in $CH_2Cl_2$ (50 ml) washed with brine (3×50 ml) dried over $MgSO_4$ and the solvent removed under vacuum to give the title compound as a white solid (1.89 g, 99%).

Example 1j

[4-(N-benzyloxyamino)-2R-isobutylsuccinyl]-L-(4-oxymethylcarboxybenzyl)-phenylalanine-N-methylamide

(4-Hydroxy-2R-isobutylsuccinyl]-L-(4-oxymethylcarboxy-benzyl)-phenylalanine-N-methylamide (1.89 g, 3.79 mmol) was dissolved in $CH_2Cl_2$ (20 ml). To the solution was added HOBT (0.63 g, 4.17 mmol), WSCDI (1.09 g, 5.6 mmol), NMM (0.58 g, 5.6 mmol) and after 15 minutes benzylhydroxylamine (0.51 g, 4.17 mmol). The reaction mixture was stirred at room temperature. After 16 hours the solvent was removed. The yellow residue was taken up in ethyl acetate whereupon white crystals precipitated out, which were collected by filtration and washed with ethyl acetate to yield the title compound as a white solid (0.58 g, 27%).

$C_{34}H_{41}N_3O_7$ MWt=603.72

$delta_H$ (250 MHz, $CDCl_3$) 8.59, (1H, m, CONHOBz), 7.37 (10H, s, CH-23-27, CH-30 to 34), 7.11 (2H, d, J-8.6 Hz, CH-9, 11), 6.80 (2H, d, J=8.6 Hz, CH-8,12), 6.47 (1H, m, CONH), 5.95 (1H, m, CONHMe), 5.21 (2H, S, $CH_2$-21), 4.87 (2H, m, $CH_2$-28), 4.63 (2H, s, $CH_2$-19), 4.52 (1H, m, CH-5), 3.02 (2H, m, $CH_2$-6a, 6b), 2.71 (3H, d+m, J=4.8 HZ, $CH_3$-13, CH-3), 2.42 (2H, m, $CH_2$-2a, 2b), 1.46 (2H, m, $CH_2$-15), 1.18 (1H, m, CH-16), 0.87, 0.84 (6H, 2d, J=6.8, 6.6 Hz, $CH_3$-17,18).

Example 1k

[4-(N-Hydroxyamino)-2R-isobutylsuccinyl]-L-(4-oxymethylcarboxylic acid)-phenylalanine-N-methylamide

[4-(N-benzyloxyamino)-2R-isobutylsuccinyl]-L-(4-oxymethylcarboxybenzyl)-phenylalanine-N-methylamide (467 mg, 0.77 mmol) was taken up in 10% cyclohexene/ ethanol (40 ml) and 20% Pd/charcoal (93 mg) added with stirring. The solution was heated under reflux and after 3 ½ hours the solution filtered through glass fibre paper. The filtrate was concentrated down under reduced pressure to give the title compound as a white solid (322 mg, 98%).

mpt=168° C.

Analysis calculated for $C_{20}H_{20}N_3O_7$ MWt=423.7;
Requires: C 56.73 H 6.90 N 9.92;
Found: C 56.52 H 6.91 N 9.59;

$delta_H$ (250 MHz, MeOD) 7.89 (1H, bd, CONHMe), 7.11 (2H, d, J=8.4 Hz, CH-9,11), 6.81 (2H, d, J=8.4 Hz, CH-8.12), 4.56 (2H, s, $CH_2$-19), 4.44 (1H, m, CH-5), 3.05 (1H, dd, J=6.4, 6.3 Hz, $CH_2$-6a), 2.87 (1H, dd, J=8.8, 9.0 Hz, $CH_2$-6b), 2.64 (3H, s,$CH_3$-13), 2.78–2.58 (1H, bm, CH-3) 2.16 (1H, dd, J=4.7, 7.8 Hz, CH-2a), 2.04 (1H, dd, J=6.5, 6.6 Hz, CH-2b), 1.36 (2H, m, $CH_2$-15), 1.13 (1H, m, CH-16), 0.81, 0.77 (6H, 2d, J=6.3 Hz, $CH_3$-17, 18).

$delta_C$ (250 MHz, DMSO) 173.34, 170.93, 169.80, 167.17, 155.8, 130.2, 129.5, 113.5, 64.1, 53.7, 40.4, 40.2, 40.0, 38.03, 35.86, 35.16, 25.10, 24.63, 22.78, 21.41.

Example 2

[4-(N-Hydroxyamino)-2R-isobutylsuccinyl]-L-(4-oxymethylcarboxy-N-methylamide) phenylalanine-N-methylamide

Example 2a

[4-(t-Butoxy)-2R-isobutylsuccinyl]-L-(4-oxymethylcarboxylic acid)-phenylalanine-N-methylamide

Utilising the procedure described in example 1 g but employing (4-(t-Butoxy)-2R-isobutylsuccinyl]-L-(4-oxymethylcarboxybenzyl)-phenylalanine-N-methylamide (from example 1h, 9.90 g, 17.85 mmol) in lieu of [4-(t-Butoxy)-2R-isobutylsuccinyl]-L-(4-benzyloxy)-phenylalanine-N-methylamide yielded, the title compound as a white solid (8.07 g, 97.3%)

$delta_H$ (250 MHz, $CDCl_3$) 7.07 (2H, d, J-8.6 Hz, CH-9, 11), 7.03 (1H, m, CONHCH), 6.79 (2H, d, J=8.6 Hz, CH-8,12), 6.70 (1H, m, CONHMe), 4.63 (1H, m, CH-5), 4.60 (2H, s, CH2-19), 2.96 (2H,d, J=7.1 Hz, $CH_2$-6), 2.66 (3H, d, J=4.8 Hz, $CH_3$-13), 2.65 (1H, s, CH-3), 2.65 (1H, s, CH-3) , 2.43 (1H, dd, J=8.5 Hz, CH2-2a) , 2.33 (1H, dd, J=5.3 Hz, CH2-2b), 1.45 (2H, m, $CH_2$-15), 1.41 (9H, s, CH3-21,22,23), 1.20 (1H, m, CH-16), 0.82 (6H, dd, J=6.3, 6.2 Hz, $CH_3$-17,18).

$delta_C$ (250 MHz, $CDCl_3$) 174.1, 170.7, 170.2, 155.3, 128.9, 118.4, 113.3, 79.6, 76.1–75.1, 63.7, 53.4, 39.8, 39.6, 36.7, 35.8, 26.6, 24.8, 24.2, 21.3, 20.8.

Example 2b

[4-(t-Butoxy)-2R-isobutylsuccinyl]-L-(4-oxymethylcarboxy-N-methylamide)-phenylalanine-N-methylamide

[4-(t-Butoxy)-2R-isobutylsuccinyl)-L-(4-oxymethylcarboxylic acid)-phenylalanine-N-methylamide (0.5 g, 1.07 mmol) was dissolved in $CH_2Cl_2$ (100 ml). At 0° C. pentafluorophenol (0.4 g, 2.15 mmol), WSCDI (0.26 g, 1.3 mmol) and N-methylmorpholine (0.11 g, 1.1 mmol) were added. After 15 minutes 8M methylamine in ethanol (0.25 g, 2.7 mmol) was added dropwise. The solution was allowed to warm to ambient temperature and stirred for 12 hours. A white solid of $MeNH_2$·HCl precipitated out, but was not collected. The reaction solution was washed with 1M HCl (100 ml), 1M $Na_2CO_3$ (100 ml) and brine (100 ml). The $CH_2Cl_2$ layer was dried over $MgSO_4$ and the solvent removed under reduced pressure to give the title compound as a white solid (0.44 g, 86%).

delta$_H$ (250 MHz, CDCl$_3$) 7.19 (2H, d, J=8.6 Hz, CH-9, 11), 6.84 (2H, d, J=8.6 Hz, CH-8,12), 6.60 (1H, m, CONHMe), 6.27 (1H, d,J=7.8 Hz, CONH), 5.99 (1H, m, CONHMe), 4.52 to 4.46 (3H, s+q, CH-5, CH$_2$-19), 3.09 (2H, m, CH$_2$-6a,6b), 2.92 (3H, d, J=4.8 Hz, CH$_3$-21), 2.72 (3H, d, J=4.8 Hz, CH$_3$-13), 2.61 (1H, m, CH-3), 2.46 (2H, m, CH$_2$-2a, 2b), 1.45 (11H, s+m, CH$_3$-23, 24, 25, CH$_2$-15) 1.20 (1H, m, CH-16), 0.87, 0.84 (6H, 2d, J=6.3 Hz, CH$_3$-17,18).

Example 2c

[4-(N-Hydroxyamino)-2R-isobutylsuccinyl]-L-(4-oxymethylcarboxy-N-methylamide)phenylalanine-N-methylamide The title compound was prepared from [4-(t-Butoxy)-2R-isobutylsuccinyl]-L-(4-oxymethylcarboxy-N-methylamide)-phenylalanine-N-methylamide utilising the method described in examples 1i to 1k mpt=211° C.

Analysis calculated for C$_{21}$H$_{32}$N$_4$O$_6$ MWt=436.51;

Requires: C 57.78 H 7.39 N 12.84;

Found: C 57.30 H 7.27 N 12.56.

delta$_H$ (250 MHz, DMSO) 10.39 (1H, s, CONHOH), 8.74 (1H, s, CONHOH), 7.98 (2H, m, CONHMe), 7.85 (1H, d, J=4.7 Hz, CONH), 7.12 (2H, d, J=8.5 Hz, CH-9,11), 6.83 (2H, d, J=8.6 Hz, CH-8,12), 4.38 (2H, s, CH-19), 4.32 (1H, m, CH-5), 2.96 (1H, dd, J=5.1, 5.0 Hz, CH$_2$-6a), 2.74 (1H, dd, J=9.6, 9.7 Hz, CH$_2$-6b), 2.64 (3H, d, J=4.7 Hz, CH$_3$-21), 2.60 (1H, m, CH-3), 2.55 (3H, d, J=4.5 Hz, CH$_3$-13), 2.05 (1H, dd, J=3.7, 7.0 Hz CH$_2$-2a), 1.91 (1H, dd, J=7.5, 7.6 Hz, CH$_2$-2b), 1.28 (2H, m CH$_2$-15), 0.98 (1H, m, CH-16), 0.77, 0.72 (6H, 2d, J=6.3 Hz, CH$_3$-17,18)

delta$_C$ (250 MHz, DMSO) 173.3, 170.9, 167.6, 167.2, 155.7, 130.5, 129.6, 113.6,, 66.7, 53.7, 40.4–36.0, 35.7, 35.2, 25.1, 24.9, 24.6, 22.8, 21.4

Example 3

4-(N-Hydroxyamino)-2R-isobutylsuccinyl]-L-(4-oxymethyl carboxymethyl)-phenylalanine-N-methylamide

Example 3a 4-(t-Butoxy)-2R-isobutylsuccinyl]-L-(4-oxymethyl carboxymethyl)-phenylalanine-N-methylamide

[4-(t-Butoxy)-2R-isobutylsuccinyl]-L-(4-oxymethylcarboxylic acid) phenylalanine-N-methylamide (from example 2a, 0.5 g, 1.08 mmol) was dissolved in CH$_2$Cl$_2$ (20 ml) and cooled to 0° C. A solution of diazomethane in ether (3 ml) was added via a pipette until gas evolution ceased and the reaction solution remained a pale yellow colour. After 30 minutes the reaction mixture was treated with 10% acetic acid/ether until the solution was colourless and washed with brine (30 ml). The CH$_2$Cl$_2$ layer was dried and the solvent removed under reduced pressure to give the title compound as a white solid (0.45 g, 87%).

C$_{25}$H$_{33}$N$_2$O$_7$ MWt=478.69 delta$_H$ (250 MHz, CDCl$_3$) 7.16 (2H, d, J=8.6 Hz, CH-9, 11), 6.83 (2H, d, J=8.6 Hz, CH-8,12), 6.35 (1H, d, J=8.0 Hz, CONH), 5.91 (1H, m, CONHMe), 4.61 (2H, s, CH$_2$-19), 4.49 (1H, q, J=7.9 Hz, CH-5), 3.61 (3H, s, CH$_3$-21), 3.06 (1H, dd, J=6.2 Hz, CH$_2$-6a) , 2.96, (1H, dd, J=9.9 Hz, CH$_2$-6b), 2.71 (3H, d, T=4.8 Hz, CH$_3$-13), 2.59 (1H, m, CH-3), 2.48 (2H, m, CH$_2$-2a, 2b) , 1.53 (2H, m, CH$_2$-15), 1.44 (9H, s, CH$_3$-23,24,25), 1.25 (1H, m, CH-16), 0.86 (6H, 2d, J=6.4 Hz, CH$_3$-17,18).

Example 3b 4-(N-Hydroxyamino)-2R-isobutylsuccinyl]-L-(4-oxymethyl carboxymethyl) phenylalanine-N-methylamide The title compound was prepared from 4-(t-Butoxy)-2R-isobutylsuccinyl]-L-(4-oxymethylcarboxymethyl) phenylalanine-N-methylamide utilising the method described in examples 1i and 1k.

mpt=187° C.

Analysis calculated for C$_{21}$H$_{31}$N$_3$O$_7$ MWt=437.5;

Requires: C 57.65 H 7.14 N 9.60;

Found: C 57.63 N 7.11 N 9.27.

delta$_H$ (250 MHz, DMSO) 10.40 (1H, s, CONHOH), 8.76 (1H, s, CONHMe), 7.99 (1H, d, J=8.0 Hz, CONH), 7.86 (1H, m, CONHMe), 7.12 (2H, d, J=8.4 Hz, CH-9,11), 6.81 (2H, d, J-8.4 Hz, CH-8,12), 4.73 (2H, s, CH$_2$-19), 4.33 (1H, m, CH-5), 3.69 (3H, s, CH$_3$-21), 2.97 (1H, dd, J=4.6 Hz, CH$_2$-6a), 2.76 (1H, dd, J=9.9, 10.1 Hz, CH$_2$-6b) 2.57, 3H, d, J=4.2 Hz, CH$_3$-13), 2.62–2.56 (1H, m, CH-3), 2.07 (1H, dd, J=6.9, 6.8 Hz, CH$_2$-2a), 1.93 (1H, dd, J=7.4, 7.6 Hz, CH$_2$-2b), 1.29 (2H, m, CH$_2$-15), 1.03 (1H, m, CH-16), 0.78, 0.74 (6H, 2d, J=6.2 Hz, CH$_3$-17,18).

delta$_C$ (250 MHz, DMSO) 173.3, 170.9, 166.6, 167.2, 155.6, 130.5, 129.6, 113.6, 64.2, 53.7, 51.3, 40.3–38.1, 35.8, 35.1,25.1, 24.6, 22.7, 21.4

Example 4

[4-(N-Hydroxyamino)-2R-isobutylsuccinyl]-L-(4-oxymethylcarboxy-N-benzylamide)-phenylalanine-N-methylamide

Example 4a

[4-(t-Butoxy)-2R-isobutylsuccinyl]-L-(4-oxymethylcarboxy-N-benzylamide) -phenylalanine-N-methylamide.

Utilising the procedure described in example 2b employing benzylamine (0.25 g, 2.4 mmol) in lieu of methylamine yielded the title compound as a white solid (0.53 g, 81%).

C$_{29}$H$_{41}$N$_3$O$_6$ MWt=527 delta$_H$ (250 MHz, CDCl$_3$ 7.40–7.27 (5H, m, CH-23 to 27), 7.17 (2H, d, J=8.6 Hz, CH-9,11), 6.92 (1H, m, CONHBz), 6.85 (2H, d, J=8.6 Hz, CH-8i12), 6.29 (1H, d, J=7.8 Hz, CONH), 5.96 (1H, m, CONHMe), 4.56–4.45 (5H, m, CH-5, CH$_2$-21, CH$_2$-19), 3.04 (2H, m, CH$_2$-6), 2.70 (3H, d, J=4.8 Hz, CH$_3$-13), 2.58 (1H, m, CH-3), 2.43 (kH, dd, J=8.5 Hz, CH$_2$-2a), 2.33 (1H, dd, J=5.3 Hz, CPL2-2b), 1.45 (2H, m, CH$_2$- 15), 1.41 (9H, s, CH$_3$-23,24,25), 1.20 (1H, M, CH-16), 0.86 (6H, 2d, J=6.3, 6.2 Hz, CH$_3$-17,18).

Example 4b

[4-(N-Hydroxyamino)-2R-isobutylsuccinyl]-L-(4-oxymethylcarboxy-N-benzylamide)-phenylalanine-N-methylamide The title compound was prepared from [4-(t-Butoxy)-2R-isobutylsuccinyl]-L-(4-oxymethylenecarboxy-N-benzylamide) phenylalartine-N-methylamide utilising the method described in examples 1i to 1k.

mpt=206° C.

Analysis calculated for C$_{27}$H$_{36}$N$_4$O$_6$ MWt=512.6;

Requires: C 63.26 H 7.08 N 10.93;

Found: C 62.52 H 7.09 N 10.97.

delta$_H$ (250 MHz, DMSO) 10.41 (1H, s, CONHOH), 8.76 (1H, s, CONHOH), 8.62 (1H, t, J=6.1 Hz, CONHCHPh), 8.01 (1H, d, J=8.3 Hz, CONH), 7.87

(1H, m, CONHMe), 7.26 (5H, m, CH-23 to 27), 7.13 (2H, d, J=8.5 Hz, CH-9,11), 6.86 (2H, d, J=8.5 Hz, CH-8,12), 4.48 (2H, s, CH$_2$-19), 4.34 (2H, d, J=6.0 Hz, CH$_2$-21), 2.97 (1H, dd, J=4.5, 4.8 Hz, CH$_2$-6a), 2.76 (1H, dd, J=9.5, 9.6 Hz, CH$_2$-6b), 2.64–2.55 (1H, bm, CH-3), 2.56 (3H, d, J=4.4 Hz, CH$_3$-13) 2.06 (1H, dd, J=3.2, 7.1 Hz, CH$_2$-2a), 1.92 (1H, dd, J=7.6 Hz, CH$_2$-2b), 1.28 (2H, m, CH$_2$-15), 0.97 (1H, m, CH-16), 0.78, 0.73 (6H, 2d, J=6.3 Hz, CH$_3$-17,18).

delta$_C$ (250 MHz, DMSO) 173.5, 170.9, 167.3, 167.2, 155.7, 138.6, 130.5, 129.6, 127.8, 126.8, 126.3, 113.9, 66.6, 53.7, 41.32, 40.1–38.1, 35.2, 25.1, 24.7, 22.8, 21.4

Example 5

[4-(N-Hydroxyamino)-2R-isobutylsuccinyl]-L-(4-oxymethylcarboxy-beta-alanine)phenylalanin-N-methylamide

Example 5a

[4-(t-Butoxy)-2R-isobutylsuccinyl]-L-(4-oxymethylcarboxy-beta-alanine benzyl ester) phenylalanine-N-methylamide Utilising the procedure described in example 2b employing beta-alanine benzyl ester (0.76 g, 2.16 mmol) in lieu of methylamine yielded the title compound as a yellow oil (0.65 g, 97%).

C$_{34}$H$_{47}$N$_3$O$_8$ MWt=625 delta$_H$ (250 MHz, CDCl$_3$) 7.35 (5H, s, CH-26 to 30), 7.17 (2H, d, J=8.5 Hz, CH-9,11), 7.19 (1H, m, CONHCH$_2$), 6.82 (2H,d, J=8.5 Hz, CH-8,12), 6.33 (1H, d, J=7.8 Hz, CONH), 6.01 (1H, rd, CONHMe), 5.13 (2H, s, CH$_2$-24), 4.49 (1H, q, J=6.7, 7.6 HZ, CH-5), 4.44 (2H, s, CH$_2$-19) 3.64 (2H, q, J=6.1 Hz, CH$_2$-21), 3.06 (2H, m, CH$_2$-6a, 6b), 2.72 (3H, d, J=4.8 Hz, CH$_3$-13), 2.66–2.62 (3H, m, CH$_2$-22, CH-3), 2.50–2.39 (2H, m, CH22a,b), 1.48 (2H, m, CH$_2$-15), 1.22, (1H, m, CH-16). 0.87, 0.84 (6H, 2d, J=6.4, 6.3 Hz, CH$_3$-17, 18).

Example 5b

[4-(N-Hydroxyamino)-2R-isobutylsuccinyl]-L-(4-oxymethylcarboxy-beta-alanine)phenylalanine-N-methylamide The title compound was prepared from [4-(t-butoxy)-2R-isobutylsuccinyl]-L-(4-oxymethylcarboxy-beta-alanine benzyl ester)phenyl alanine-N-methylamide utilising the method described in examples 1i to 1k.

mpt=195° C.

Analysis calculated for C$_{23}$H$_{34}$N$_4$O$_8$ MWt=494.6;
Requires: C 55.86 H 6.93 N 11.33;
Found: C 55.94 H 6.96 N 11.51.

delta$_H$ (250 MHz, MeOD) 7.13 (2H, d, J=8.5 Hz, CH-9,11), 6.86 (2H, d, J=8.5 Hz, CH-8,12), 4.47–4.42 (1H, m, CH-5), 4.42 (2H, s, CH$_2$-19), 3.48 (2H, t, J=6.7 HZ, CH$_2$-21), 3.06 (1H, dd, J=6.4, 6.3 Hz, CH$_2$-6a), 2.85 (1H, dd, J=8.71 8.8 Hz, CH$_2$-6b), 2.80–2.64 (1H, m, CH-3), 2. 64 (3H, s, CH$_3$-13), 2.50 (2H, t, J=6.7 Hz, CH$_2$-22), 2.17 (1H, dd, J=6.5 Hz, CH$_2$-2a), 2.04 (1H, dd, J=6.5 Hz, CH$_2$-2b) 1.36 (2H, m, CH$_2$-15), 1.06 (1H, m, CH-16), 0.81, 0.77 (6H, 2d, J=6.3 Hz, CH$_3$-17,18).

delta$_C$ (250 MHz, MeOD) 177.1, 175.5, 173.9, 171.1, 170.6, 157.9, 132.0, 131.4, 115.8, 68.3, 56.2, 50.0, 49.6–47.9, 42.5, 42.4, 37.9, 36.8, 36.0, 34.6, 26.8, 26.3, 23.5, 22.

Example 6

[4-(N-Hydroxyamino)-2R-isobutylsuccinyl]-L-(4-oxymethylcarboxy-glycine methyl ester) phenylalanine-N-methylamide

Example 6a

[4-(t-Butoxy)-2R-isobutylsuccinyl]-L-4-oxymethylcarboxy-glycine methylester)-phenylalanine-N-methylamide.

Utilising the procedure described in example 2b employing glycine methyl ester hydrochloride (0.13 g, 1.07 mmol) in lieu of methylamine yielded the title compound as a white solid (0.45 g, 78.5%).

C$_{27}$H$_{41}$N$_8$O$_8$ MWt=535.64 delta$_H$ (250 MHz, CDCl$_3$) 7.17 (2H, d, J=8.6 Hz, CH-9,11), 7.15 (1H, m, CH2CONHCH$_2$), 6.83 (2H, d, J=8.6 Hz, CH-8), 6.45 (1H, d, J=8.0 Hz, CHCONHCH), 6.26 (1H, m, CONHMe), 4.53 (1H, m, CH-5), 4.48 (2H, s, CH$_2$-19), 4.13 (2H, d, J=6.3 Hz, CH$_2$-21), 3.76 (3H, S, CH$_3$-23), 3.04 (2H, m, CH$_2$-6), 2.72 (3H, d, J=4.8 Hz, CH$_3$-13), 2.51 (1H, m, CH-3), 2.42 (2H, m. CH$_2$-2), 1.47 (2H, m, CH$_2$-15), 1.43 (9H, S, CH$_3$-24,25,26), 1.19 (1H, M, CH-16), 0.83 (6H, dd, J=6.3 Hz, CH$_3$-17,18).

Example 6b

[4-(N-Hydroxyamino)-2R-isobutylsuccinyl]-L-(4-oxymethylcarboxy-glycinemethylester)-phenylalanine-N-methylamide The title compound was prepared from [4-(t-Butoxy)-2R-isobutylsuccinyl]-L-4-oxymethyl carboxy-glycine methyl ester)-phenylalanine-N-methylamide utilising the method described in examples 1i to 1k.

mpt=180°–185° C.

Analysis calculated for C$_{23}$H$_{34}$N$_4$O$_8$ MWt=494.55;
Requires: C 55.86 H 6.93 N 11.33;
Found: C 53.45 H 6.83 N 11.50.

delta$_H$ (250 MHz, MeOD) 7.14 (2H, d, J 8.6 Hz, CH-9,11)6.89, (2H, d, J=8.6 Hz, CH-8,12), 4.49 (2H,s, CH$_2$-19), 4.44 (1H, m, CH-5), 3.99 (2H, s, CH$_2$-21), 3.69 (3H, s, CH$_3$-23), 3.11–2.81 (2H, m, CH$_2$-6), 2.72–2.63 (1H, m, CH-3), 2.64 (3H, s, CH$_3$-13), 2.21 (1H,dd, J=7.8 Hz, CH$_2$-2a), 2.04 (1H, dd, J=6.7,6.6 Hz, CH$_2$-2b), 1.35 (2H, m, CH$_2$-15) 1.05 (1H, m, CH-16), 0.79 (6H, dd, J=6.4 Hz,-CH$_3$-17,18).

delta$_C$ (250 MHz, MeOD) 177.1, 173.9, 171.8, 171.6, 170.6, 158.0, 132.1, 131.4, 115.9, 68.3, 56.3, 52.7, 50.0–48.0, 42.6, 42.4, 41.5, 37.9, 36.8, 26.8, 26.3, 22.3

Example 7

[4-(N-Hydroxyamino)-2R-isobutylsuccinyl]-L-(4-oxymethylcarboxyethyl)-phenylalanine-N-methylamide

Example 7a

[4-(t-Butoxy)-2R-isobutylsuccinyl]-L-(4-oxymethyl carboboxyethyl)-phenylalanine-N-methylamide When the procedure described in example 1 g was utilised employing (4-(t-butoxy)-2R-isobutylsuccinyl]-L-(4-oxymethylcarboxybenzyl ester) phenylalanine-N-methylamide (from example 1h 9.10 g, 16.41 mmol) in lieu of [4-(t-Butoxy)-2R-isobutylsuccinyl]-L-(4-benzyloxy) phenylalanine-N-methylamide a transesterification reaction occurred and an ethyl group was transferred from the solvent to the reactant molecule. The reaction yielded after chromatography (flash silica, 100% ethyl acetate) the title compound as a white solid (0.51 g, 6.3%)

$C_{26}H_{46}N_2O_7$ MWt=492.62

$^1$Hnmr delta$_H$ (250 MHz, CDCl$_3$) 7.09 (2H, d, J=8.6 Hz, CH-9,11),-6.77 (2H, d, J=8.6 Hz, CH-8,12), 6.68 (1H, d, J=8.8 Hz, CONHCH), 6.57 (1H, M, CONHMe), 4.55 (1H, m, CH-5), 4.53 (2H, S, CH$_2$-19), 4.21 (2H, q, J=7.1 Hz, CH$_2$-21), 2.97 (2H, m, CH 2-6), 2.72-2.52 (1H, M, CH-3), 2.65 (3H, d, J=4.8 Hz, CH$_3$-13), 2.43 (1H, dd, J=7.8 Hz, CH$_2$-2a), 2.27 (1H, dd, J=6.8 Hz, CH 2-2b), 1.42 (2H, m, CH$_2$-15), 1.37 (9H, s, CH$_3$-23,24,25), 1.25 (3H, t, J=7.1 Hz, CH$_3$-22), 1.14 (1H, m, CH-16), 0.78 (6H, dd, J=6.4 Hz, CH$_3$-17,18).

Example 7b

[4-(N-Hydroxyamino)-2R-isobutylsuccinyl]-L-(4-oxymethyl carboxyethyl)-phenylalanine-N-methylgmide.

The title compound was prepared from [4-(t-butoxy)-2R-isobutylsuccinyl]-L-(4-oxymethylcarboxyethyl)-phenylalanine-N-methylamide utilising the method described in examples 1i to 1k.

mpt 185° C.

Analysis calculated for $C_2H_{33}N_3O_7$ MWt=451.52;
Requires: C 58.52 H 7.37 N 9.31;
Found: C 58.54 H 7.28 N 9.26.

delta$_H$ (250 MHz, MeOD) 7.11 (2H, d, J=8.6 Hz, CH-9,11), 6.79 (2H,d, J=8.6 Hz, CH-8,12), 4.61 (2H, s, CH$_2$-19), 4.43 (1H, m, CH-5), 4.19 (2H, q, J=7.1, 7.2 Hz,CH$_2$-21), 3.05 (1H, dd, J=6.4, 6.4 Hz, CH$_2$-6a), 2.81 (1H, dd, J=9.1, 8.9 Hz, CH$_2$-6b), 2.64 (3H, s, CH -13), 2.78-2.58 (1H, m, CH-3) , 2.12 (1H, dd, J=7.8, 7.9 Hz, CH$_2$-2a), 2.06 (1H, dd, J=6.7, 6.8 Hz, CH$_2$-2b), 1.31 (2H,m, CH$_2$-15), 1.24 (3H, t, J=7.1 Hz, CH$_3$-22) 1.09 (1H, m, CH-16), 0.79 (6H, dd, J=6.4 Hz, CH$_3$-17, 18).

delta$_C$ (250 MHz, MeOD) 177.2, 174.0, 171.0, 170.6, 158.1, 131.8, 131.2, 115.6, 66.4, 62.4, 56.4, 50.1,−48.0, 42.6, 42.4, 38.1, 36.9, 26.8, 26.4, 23.6, 22.4, 14.

Example 8

[4-(N-Hydroxyamino)-2R-isobutylsuccinyl]-L-(4-oxymethyl carboxyglycine)phenylalanine-N-methyl

Example 8a

[4-(t-Butoxycarbonvl)-2R-isobutylsuccinyl]-L-(4-oxymethylcarboxyglycine benzyl ester)-phenylalanine-N-methylamide Utilising the procedure described in example 2b employing glycine benzyl ester hydrochloride (0.24 g, 1.21 mmol) in lieu of methylamine yielded the title compound as a white solid (0.55 g, 89.5%).

$C_{33}H_{45}N_3O_8$ MWt=611.74 delta$_H$(250 MHz, CDCl$_3$) 7.38 (5H, m, CH-24 to 29), 7.22-7.11 (1H, m, CONHCH$_2$CO$_2$Bz), 7.17 (2H, d, J=7.76 Hz, CH-9, 11), 6.84 (2H, d, J=7.6 Hz, CH-8, 12), 6.47 (1H, d, J-8.1 Hz, CHCONHCH), 6.24 (1H, m, CONHMe), 5.19 (2H, s, CH 2-23), 4.62–4.42 (1H, m,CH-5), 4.48 (2H, s, CH 2-19), 4.16 (2H, d, J=6.5 Hz, CH$_2$-21), 3.05 (2H, m, CH$_2$-6), 2.77–2.55 (1H, m, CH-3), 2.73 (3H, d, J=4.2 Hz, CH$_3$-13), 2.53 (1H, dd, J=6.6 Hz, CH$_2$-2a), 2.35 (1H, dd, J=5.3 Hz, CH$_2$-2b), 1.55-1.37 (2H, m, CH 2-15), 1.45 (9H, s, CH$_3$-30,31,32), 1.22, (1H, m, CH-16), 0.97 (6H, m, CH$_3$-17,18).

Example 8b

[4-(N-Hydroxyamino)-2R-isobutylsuccinyl]-L-(4-oxymethylcarboxyglycine)phenylalanine-N-methylamide The title compound was prepared from [4-(t-butoxycarbonyl)-2R-isobutylsuccinyl]-L-(4-oxymethylcarboxyglycine benzyl ester)-phenylalanine-N-methylamide utilising the method described in examples 1i to 1k.

mpt=142.5° C.

Analysis calculated for $C_{22}H_{32}N_4O_8$ MWt=480.52;
Requires: C 54.99; H 6.71 N 11.66;
Found: C 54.19; H 6.87 N 10.96.

delta$_H$ (250 MHz, DMSO) 10.42 (1H, s, CONHOH), 8.32 (1H, m, CONHCH$_2$CO$_2$H), 8.01 (1H, d, J=8.1 Hz, CHCONHCH), 7.87 (1H, m, CONHMe), 7.13 (2H, d, J=7.6Hz, CH-9,11), 6.87 (2H, d, J=7.3 Hz, CH-8,12), 4.46 (2H, s, CH$_2$-21), 4.33 (1H, M, CH-5), 3.80 (2H, d, J=5.5 Hz, CH 2-19), 2.96 (1H, dd, J=4.6, 4.5 Hz, CH$_2$-6a), 2.75 (1H, m, CH$_2$-6b), 2.56 (3H, s, CH$_3$-13), 2.68-2.43 (1H, m, CH-3), 2.05 (1H, dd, J=7.0, 6.6 Hz, CH$_2$-2a), 1.91 (1H, dd, J=5.3 Hz, CH$_2$-2b), 1.26 (2H, m, CH$_2$-15), 1.05 (1H, m, CH-16), 0.75 (6H, dd, J=5.7 Hz, CH$_3$-17,18).

delta$_C$ (250 MHz, DMSO) 173.4, 170.9, 170.5, 167.6, 167.2, 155.6, 130.6, 129.6, 113.9, 66.5, 53.7, 40.3, 40.2, 39.7-38.4, 5.9, 35.2, 25.9, 25.1, 22.8, 21.4

Example 9

[4-(N-Hydroxyamino)-2R-isobutylsuccinyl]-L-(4-oxymethyl carboxy-NmN-dimethylamide)-phenylalanine-N-methylamide

Example 9a

[4-(t-Butoxy)-2R-isobutylsuccinyl]-L-(4-oxymethyl carboxy-N,N-dimethylamide)-phenylalanine-N-methylamide Utilising the procedure described in example 2b employing dimethylamine hydrochloride (0.11 g, 1.30 mmol) in lieu of methylamine yielded the title compound as a white solid (0.49 g, 92.3%).

$C_{26}H_{41}N_3O_6$ MWt=491.63 delta$_H$ (250 MHz, CDCl$_3$) 7.13 (2H, d, J=8.5 Hz, CH-9,11), 6.85 (2H, d, J=8.5 Hz, CH-8,12), 6.42 (1H, d, J=8.0 Hz, CHCONHCH), 6.19 (1H, m, CONHMe), 4.63 (2H, s, CH$_2$-19), 4.50 (1H, m, CH-5), 3.12–2.82 (2H, m, CH$_2$-6), 3.07 (3H, s, CH$_3$-22), 2.96 (3H, s, CH$_3$-22), 2.68 (3H, d, J=4.5 HZ, CH$_3$-13), 2.62 (1H, m, CH-3), 2.52 (1H, dd, J=8.5 Hz, CH$_2$-2a), 2.33 (1H, dd, J=4.5 Hz, CH$_2$-2b), 1.55-1.35 (2H, m, CH$_2$-15), 1.42 (9H, s, CH$_3$-23,24,25), 1.19 (1H, m, CH-16), 0.83 (6H, dd, J=6.3 Hz, CH$_3$-17,18).

Example 9b

[4-(N-Hydroxyamino)-2-isobutylsuccinyl]-L-(4-oxymethyl carboxy-N,N-dimethylamide)-phenylalanine-N-methylamide The title compound was prepared from [4-(t-Butoxy)-2R-isobutylsuccinyl]-L-(4-oxymethyl-carboxy-N,N-dimethylamide)-phenylalahine-N-methylamide utilising the method described in examples 1i to 1k.

mpt=197° C.

Analysis calculated for $C_{22}H_{34}N_4O_6$ MWt=450.54;
Requires: C 58.65 H 7.61 N 12.44;

Found: C 58.58 H 7.54 N 12.33.

$\delta_H$ (150 MHz, DMSO) 0.42 (1H, s, CONHOH), 8.77 (1H, s, CONHOH), 7.99 (1H, d, J=8.0 Hz, CHCONHCH), 7.87 (1H, m, CONHMe), 7.09 (2H, d, J=8.5 Hz, CH-9,11), 6.78 (2H, d, J=8.5Hz, CH-8,12), 4.71 (2H, s, CH$_2$-19), 4.32 (1H, m, CH-5), 2.98 (3H, s, CH$_3$-21), 2.94 (1H, m, CH$_2$-6a), 2.83 (3H, s, CH$_3$-22), 2.73 (1H, m, CH$_2$-6b), 2.55 (3H, m, CH$_3$-13), 2.68-2.45 (1H, m, CH-3), 2.01 (1H, dd, J-6.8 Hz, CH$_2$-2a), 1.91 (1H, dd, J=6.8 Hz, CH$_2$-2b), 1.28 (2H, m, CH$_2$-15), 0.99 (1H, m, CH-16), 0.74 (6H, dd, J=6.3, 6.2 Hz, CH$_3$-17,18).

$\delta_C$ (250 MHz, CDCl$_3$) 173.4, 170.9, 167.2, 166.8, 156.1, 130.0, 129.4, 113.7, 65.5, 53.7, 40.9-38.0, 35.9, 35.2, 34.5, 25.1, 24.6, 21.4

Example 10

[4-(N-Hydroxyamino)-2R-isobutylsuccinl](4-acetamido) phenylalanine-N-methylamide

Example 10a p-Aminophenylalanine methyl ester

To a stirred solution of p-aminophenylalanine (2.05 g, 9.9 mmol) in methanol (100ml) at 0° C. was added thionyl chloride (20ml) dropwise. Upon complete addition the reaction mixture was heated under reflux. After 24 hours the reaction mixture was cooled and reduced under pressure to give a brown oil. The brown oil was taken up in ethyl acetate (200 ml) and washed with saturated sodium bicarbonate solution (200 ml). The aqueous layer was further extracted with ethyl acetate (5×200 ml). The combined organic layer was dried over MgSO$_4$ and reduced under pressure to yield the title compound as a brown solid (1.7 g, 88.5%).

$\delta_H$ (250 MHz, CDCl$_3$) 6.95 (2H, d, Ar-H), 6.60 (2H, d, Ar-H, 3.70 (3H, s, CO$_2$CH$_3$), 3.65 (1H, dd, CHCO$_2$CH$_3$), 2.95 (1H, dd, CH$_2$Ph), 2.75 (1H, dd, CH$_2$Ph), 2.60 (4H, bm, 2NH2).

Example 10b p-Aminophenylalanine-N-methylamide

To a stirred solution of p-aminophenylalanine methyl ester (1.7 g, 8.8 mmol) in ethanol (150 ml) was added methylamine in ethanol (33%/8M) (100 ml). After stirring at room temperature for 24 hours the reaction mixture was reduced under pressure to yield the title compound as a brown solid (1.7 g, 100%)

$\delta_H$ (250 MHz, CDCl$_3$) 6.90 (2H, d, Ar-H), 6.55 (2H, d, Ar-H), 3.40 (1H, dd, CHCONHCH$_3$), 3.00 (1H, dd, CH$_2$Ph) 2.70 (,3H, d, CONHCH$_3$), 250 (1H, dd, CH$_2$Ph).

Example 10c

[4-(t-Butoxy)-2R-isobutylsuccinyll-L-4-amino-phenylalanine-N-methylamide

Utilising the procedure described in example 1f but employing p-aminophenylalanine-N-methylamide (1,7 g, 8.79 mmol) in lieu of O-benzyl tyrosine-N-methylamide yielded the title compound as a light brown oil (1.39 g, 38%)

$\delta_H$ (250 MHz, CDCl$_3$) 7.00 (2H, d, J=8.3 Hz, CH-9,11), 6.60 (2H, d, J=8.3 Hz, CH-8, 12), 6.45 (1H, d, J=7.8 Hz, CONHCH), 6.10 (1H, d, J=4.7 Hz, CONHMe), 4.50 (1H, q, J=7.9 Hz, CH-5), 2.95 (2H, dq, j,=13.7, 7.9HZ, CH$_2$-2), 2.67 (3H, d, J=4.9 Hz, CH$_3$-13, 260 (1H, M, CH-3), 2.45 (2H, dq, J=16.3, 5.1 Hz, CH$_2$-6), 1.45 (2H, m, CH$_2$-15), 1.40 (9H, S, C(CH$_3$)$_3$), 1.20 (1H, M, CH-16), 0.85 (6H, dd, J=6.3, 7.9 Hz, CH$_3$-17, 18). $\delta_C$ (250 MHz, CDCl$_3$) 174.6, 171.6, 171.5, 145.1, 130.1, 126.6, 115.3, 80.9, 54.9, 41.0, 38.2, 37.4, 28.0, 26.0, 25.6, 22.6, 22.3

Example 10d

[4-(t-Butoxy)-2R-isobutylsuccinyl]-L-(4-acetamidoi phenylalanine-N-methylamide

A solution of [4-(t-Butoxy)-2R-isobutylsuccinyl-L-4-amino phenylalanine-N-methylamide (0.7 g, 1.73 mmol), acetic anhydride (0.2 g, 0.18 ml, 1.9 mmol), DMAP (catalytic amount) and triethylamine (0.2 g, 0.3 ml, 1.9 mmol) in CH$_2$Cl$_2$ (10 ml), was stirred at room temperature. After 24 hours the reaction mixture was washed with 2M HCl (20 ml×2) and brine (20 ml). The CH$_2$Cl$_2$ layer was dried over MGSO$_4$ and reduced under pressure to yield the title compound as a light brown solid (0.77 g, 99.4%).

$\delta_H$ (250 MHz, CDCl$_3$) 8.35 (1H, bs, NHCOCH3), 7.40 (2H, d, J=8.4 Hz, CH-9,11), 7.10 (2H, d, J=8.4 Hz, CH-8,12), 4.55 (JH, dd, J=7.7, 7.1 Hz, CH-5), 2.65 (3H, d, J=4.7 Hz, CH$_3$-13), 2.60 (1H, m, CH-3), 2.40 (2H, m, CH$_2$-2), 1.45 (2H, m, CH$_2$-15), 1.40 (9H, s,C(CH$_3$)$_3$), 1.15 (1H, m, CH-16), 0;80 (6H, dd, J=6.2, 3.0 Hz, CH$_3$-17,18).

Example 10e

[4-(N-Hydroxyamino)-2R-isobutylsuccinyl]-L-(4-acetamido)phenylalanine-N-methylamide The title compound was prepared from [4-(t-Butoxy)-2R-isobutylsuccinyl)-L-(4-acetamido) phenylalanine-N-methylamide utilising the method described in examples 1i to 1k.

Analysis calculated C$_{20}$H$_{30}$N$_4$O$_5$ MWt=406.48;
Requires: C59.09 H7.44 N 13.78;
Found: C58.90 H7.38 N 13.70.

$\delta_H$ (250 MHz, MeOD) 7.42 (2H, d, J=8.4 Hz, CH-9,11), 7.13 (2H, d, J=8.4 Hz, CH-8,12), 4.46 (1H, dd, J=9.0, 6.4 Hz, CH-5), 3.10 (1H, dd, J=13.8, 9.1 Hz, CH$_2$-6a), 2.86 (1H, dd, J=13.8, 9.1 Hz, CH$_2$-6b), 2.65 (3H, s, CH$_3$-13), 2.60 (1H, m, CH-3), 2.19 (1H, dd, J=14.5, 6.5 Hz, CH$_2$-2a), 2.05 (3H, s, NHCOCH3), 2.04 (1H, dd J=14.5, 6.5 Hz, CH$_2$-2b), 1.40 (1H, m, CH$_2$-15a), 1.30 (1H, m, CH-16), 1.05 (1H, m, CH$_2$-15b), 0.77 (6H, dd, J=6.4, 5.4 Hz, CH$_3$-17,18).

$\delta_C$ (250 MHz, MeOD) 177.1, 173.9, 171.5, 170.7, 138.5, 134.5, 130.6, 121.1, 42.7, 42.4, 38.1, 36.8, 26.7, 26.3, 23.7, 23.5, 22.3

Example 11

2a), 1. 91 (1H, dd, J=6.8 Hz, CH -2b)
[4-(N-Hydroxyamino)-2R-isobutylsuccinyl]-L-(4-cyano) phenylalanine-N-methylamide

Example 11a

N-(N-dimethylthioimidate)-L-(4-cyano)-phenylalaninyl)(2R)-bornane-10,2-sultam

To a solution of N-((N-dimethylthioimidate)-glycinyl)(2R)-bornane-10,2-sultam (Oppolzer's chiral glycine equivalent, 10 g, 26.6 mmol) in dry THF (50 ml) under an argon atmosphere at −65° C. was added n-butyllithium (1.36M, 19.5 ml, 26.6 mmol). After stirring the reaction mixture at −65° C. for 30 mins (20 ml) alpha-bromotolunitrile (5.21 g, 26.6 mmol) in dry THF (20 ml) was added via syringe followed by addition of HMPA (20 ml) via cannula. The reaction mixture was kept at −65° C. for 1 hour, then allowed to warm to ambient temperature overnight. The reaction mixture was quenched with saturated NH₄Cl solution (5 ml) and the THF removed under pressure. The residue was dissolved in ethyl acetate and washed with 0.5M HCl (50 ml) and H₂O (2×50 ml). The ethyl acetate layer was dried over MgSO₄ and the solvent removed under pressure to yield the title compound as a yellow solid (0.7 g, 93%).

$C_{23}H_{29}N_3O_3S_3$ MWt=491.67 delta$_H$ (250 MHz, CDCl$_3$) 7.56 (2H, d, J=8.2 Hz, Ar-H), 7.41 (2H, d, J=8.2 Hz, Ar-H), 5.18 (1H, dd, J=8.12, 5.6 Hz, CHNC(SCH$_3$)$_2$), 3.90 (1H, dd, J=8.6, 4.7 Hz, CHNSO$_2$), 3.46 (2H, dd, J=3.2Hz, CH$_2$SO$_2$, 3.39 (1H, dd, J-12.7, 5.6 Hz, CH$_2$Ph), 3.12 (1H, dd, J=12.7, 8.3 Hz, CH$_2$Ph), 2.48 (3H, s, SCH$_3$) 2.40 (3H, s, SCH$_3$), 2.13 to 1.77 (5H, m, CH$_2$+CH$_2$+CH), 1.47 to 1.23 (2H, m, CH$_2$) 0.95 (3H, s, CH$_3$), 0.93 (3H, s, CH$_3$).

delta$_C$ (250 MHz, CDCl$_3$) 170.14, 163.85, 143.00, 131.78, 130.67, 118.93, 110.37, 65.85, 65.23, 53.10, 48.43, 47.62, 44.43, 40.23, 38.17, 32.69, 26.30, 20.42, 19.70, 15.25, 14.82.

Example 11b

N-((4-cyano) phenylalaninyl)-(2R)-bornane-10,2-sultam

Hydrochloric acid (0.2M, 125 ml, 250 mmol) was added to a stirred solution of N-((N-dimethylthioimidate)-L-(4-cyano)phenylalaninyl)-(2R)-bornane-10,2-sultam (12.8 g, 22.8 mmol) in THF (250 ml). After stirring the reaction mixture for 24 hours at room temperature, the THF was removed under pressure and the residue partitioned between water and CH$_2$Cl$_2$. The aqueous layer was basified with saturated sodium bicarbonate solution and extracted with ethyl acetate (3×100 ml). The combined ethyl acetate layers were dried over MgSO$_4$ and the solvent removed under pressure to yield the title compound as a white solid (3.21 g, 36.3%).

$C_{20}H_{25}N_3O_3S$ MWt=387.48

EXAMPLE 11c

N-((N-tertbutoxycarbonyl)-(4-cyano)-phenylalaninyl)(2R)-bornane-10,2-sultam

A solution of N-((4-cyano)phenylalaninyl)-(2R)-bornane-10,2-sultam (4.60 g, 11.9 mmol) in CH$_2$Cl$_2$ (20 ml) was treated with Boc-anhydride (2.58 g, 13.0 mmol) and triethylamine (1.32 g, 13.0 mmol). After stirring the reaction mixture for 16 hours at room temperature, it was washed with 1M citric acid (2×50 ml). The organic layer was dried over MGSO$_4$ and the solvent removed under pressure to yield the title compound as a pale yellow foam (4.46 g, 77%)

$C_{25}H_{25}N_3O_5S$ MWt=59 delta$_H$ (250 MHz, CDCl$_3$) 7.56 (2H, d, J=8.2 Hz, Ar-H), 7.38 (2H, d, J=8.0 Hz, Ar-H), 5.13 (2H, bm, NH+CHNH), 3.88 (1H, dd, J=7.1, 5.0 Hz, CHNSO$_2$), 3.51 (2H, dd, J=2.1 Hz, CH$_2$SO$_2$) , 3.38 (1H, bdd, CH$_2$Ph) , 2.80 (1H, bdd, CH$_2$Ph) 2.14 to 1.80 (5H, bm, CH$_2$+CH$_2$+CH), 1.43 to 1.17 (11H, bm, C(CH$_3$)$_3$+CH$_2$), 1.04 (3H, s, CH$_3$), 0.97 (3H, s, CH$_3$).

Example 11d

N-Boc-4-cyanophenylalanine

A solution of N-((N-tertbutoxycarbonyl)-(4-cyano) phenylalaninyl)-(2R)-bornane-10,2-sultam (8.78 g, 18.0 mmol) in THF (120 ml) was treated with a solution of Li(OH)$_2$ (3.02 gm 72.0 mmol) in H$_2$O (60 ml). After stirring the reaction mixture for 16 hours at room temperature the THF was removed under pressure. The residue was taken up in CH$_2$Cl$_2$ (75 ml), the aqueous layer separated and further extracted with CH$_2$Cl$_2$ (2×75 ml). The aqueous layer was then acidified with 2M HCl to pH2 and extracted with ethyl acetate (3×75 ml). The combined ethyl acetate layers were dried over MgSO$_4$ and the solvent removed under pressure to yield the title compound as a pale yellow solid (4.47 g, 85.5%).

$C_{15}H_{18}N_2O_4$ MWt=290.31 delta$_H$ (250 MHz, CDCl$_3$/DMSO) 7.52, (2H, d, Ar-H) 7.26 (2H, d, Ar-H), 5.16 (1H, bd, NH), 4.48 (1H, dd, CHNH, 3.22 (1H, dd, CH$_2$Ph), 3.02 (1H, dd, CH$_2$Ph), 1.36 (9H, bs, C(CH$_3$)$_3$).

Example 11e

N-Boc-4-cyanophenylalanine-N-methylamide

A solution of N-Boc-4-cyanophenylalanine (1.92 g, 6.6 mmol) and pentafluorophenol (2.43 g, 13.2 mmol) in CH$_2$Cl$_2$ (30 ml) at 0° C. was treated with 4-methylmorpholine (0.74 g, 7.3 mmol). After stirring the reaction mixture for 3 hours, 8M methylazine in ethanol (15 ml, 19.8 mmol) was added and the reaction mixture left to stir at room temperature for 16 hours. The solvent was removed under pressure, the residue dissolved in CH$_2$Cl$_2$ (50 ml) and washed with saturated sodium bicarbonate (2×50 ml) , 1M citric acid (2×50 ml) and brine (50 ml). The CH$_2$Cl$_2$ layer was dried over MgSO$_4$ and the solvent removed under pressure to yield the title compound as a white solid (1.84 g, 92%).

$C_{16}H_{21}N_3O_3$ MWt=303.35 delta$_H$ (250 MHz, CDCl$_3$) 7.60 (2H, d, J=8.3 Hz, Ar-H), 7.33 (2H, d, J=8.4 Hz, Ar-H), 6.00 (1H, bd, NiI), 5.04 (1H, bd, CONHCH$_3$) 4.35 (1H, bd, CHNH), 3.21 (1H, dd, CH$_2$Ph) , 3.04 (1H, dd, CH$_2$Ph), 2.76 (3H, d, J=4.9 Hz CH$_3$), 1.39 (9H, s, C(CH$_3$)$_3$)

Example 11f 4-cyanophenylalanine-N-Methylamide

Utilising the procedure described in example 1e but employing N-Boc-4-cyano-phenylalanine-N-methylamide (3.36 g, 11.1 mmol) in lieu Of N-Boc-O-benzyl tyrosine methylamide yielded the title compound as the TFA salt (3.49 g, 100%).

Example 11g

[4-(t-Butoxy)-2R-isobutylsuccinyl-L-(4-cyano)-phenylalanine-N-methylamide

Utilising the procedure described in example if but employing 4-cyanophenylalanine-N-methylamide TFA salt (3.4 g, 11.1 mmol) in lieu of O-benzyl tyrosine N-methylamide and 4-methylmorpholine (2.24 g, 22.2 mmol) yielded the title compound as an off whits solid (3.11 g, 67.5%)

$C_{23}H_{33}N_3O_4$ MWt=415.51 delta$_H$ (250 MHz, CDCl$_3$) 7.59 (2H, d, T=8.2 Hz, CH-9, 11), 7.37 (2H, d, J=8.1 Hz, CH-8, 12), 6.29 (1H, bd, CONH) 6.23 (1H, bd, CONHCH$_3$), 4.60 (1H, dd, CH-5), 3.26 (1H, dd, CH$_2$-6a), 3.17 (1H, dd, CH$_2$-6b), 2.75 (3ii, d, J=4.8 Hz, CH 3-13), 2.49 (1H, dd, CH$_2$-2, 2.37 (1H, dd, CH$_2$-2b), 1.57 to 1.30 (2H, m, CH -15a+CH-16, (9H, s, C(CH$_3$)$_3$), 1.30 to 1.10 (1H, m, CH$_2$-15b) 0.97 (3H, d, j=6.9 Hz, CH$_3$-17), 0.84 (3H, d, J=7.1 Hz, CH$_3$-18)

Example 11h

[4-N-Hydroxyamino)-2R-isobutylsuccinyl]-L-(4-cyano)phenylalanine-N-methylamide

The title compound was prepared from 4-(t-butoxy)-2R-isobutylsuccinyl]-L-(4-cyano)phenylalanine-N-methylamide utilising the method described in examples 1i to 1k.

Analysis calculated for $C_{19}H_{26}N_4O_4$ MWt=374.43;
Calculated: C 60.94 H 7.00 N 14.96;
Found: C 61.18 H 7.21 N 14.14.

$delta_H$ (250 MH, MeOD) 7.61 (2H, d, J=8.2 Hz, $CH_2$-9, 11), 7.38 (2H, d, J=8.2 Hz, $CH_2$-8, 12), 7.05 (1H, s, NH), 4.53 (1H, dd, J=9.1, 6.0 Hz, CH-5), 3.23 (1H, dd, J=14.0, 5.9 Hz, $CH_2$-6b), 3.01 (1H, dd, J=9.1 Hz, $CH_2$-6a), 2.66 (3H, s, $CH_3$-13), 2.20 (1H, dd, J=8.0 m 2.0 Hz, $CH_2$-2a), 2.07 (1H, dd, J=18.0, 6.0 Hz, $CH_2$-2b), 1.36 (1H, m, $CH_2$-15a), 1.24 (1H, m, CH-16), 1.07 (1H, m, $CH_2$-15b), 0.80 (3H, d, J=6.3 Hz, $CH_3$-17), 0.76 (3H, d, J=6.4 Hz, $CH_3$-18).

$delta_C$ (250 MHz, MeOD) 177.13, 173.29, 170.59, 145.02, 133.25, 131.38, 119.73, 111.48, 55.51, 42.60, 38.56, 36.68, 26.70, 26.30, 23.46, 22.25, 21.05

What is claimed is:

1. A compound of the formula:

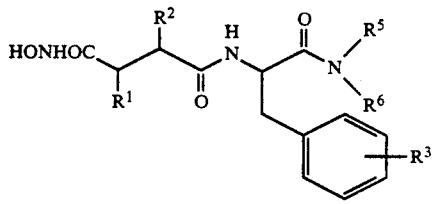

wherein
$R^1$ is hydrogen, $C_1$–$C_6$ alkyl, phenyl, or phenyl ($C_1$–$C_6$ alkyl);
wherein
$R^2$ is hydrogen, $C_1$–$C_6$ alkyl, $C_2$–$C_6$ alkenyl, phenyl ($C_1$–$C_6$ alkyl) or cycloalkyl ($C_1$–$C_6$ alkyl);
wherein
$R^5$ is hydrogen or $C_1$–$C_6$ alkyl, $R^6$ is hydrogen or methyl, and $R^3$ represents —O—$CH_2$—CO—$R^8$ where $R^8$ is hydroxyl, $C_1$–$C_6$ alkyloxy, amino, amino substituted with 1 or 2 $C_1$–$C_6$ alkyl, or benzyl groups, or salts thereof.

2. A compound as claimed in claim 1, in which the chiral center adjacent to the substituent $R^2$ has R stereochemistry.

3. A compound as claimed in claim 1, in which the chiral center adjacent to the substituted benzyl group has S stereochemistry.

4. A compound as claimed in claim 1, in which the chiral center adjacent to $R^1$ has S stereochemistry.

5. A compound of the formula:

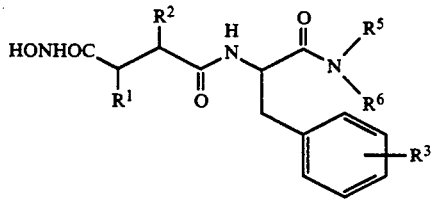

where $R^1$, $R^2$, $R^5$ are hydrogen or $C_1$–$C_6$ alkyl, $R^6$ is hydrogen or methyl, and $R^3$ represents —O—$CH_2$—CO—$R^8$ where $R^8$ is hydroxyl, or $C_1$–$C_6$ alkyloxy.

6. A compound according to claim 1 which is selected from the group consisting of:
N-[4-Hydroxyamino-4-oxo-2R-isobutylbutanoy]-L-4-(carboxymethoxy) phenylalanine-N-methylamide;
N-[4-Hydroxyamino-4-oxo-2R-isobutylbutanoy]-L-4-((N-methylamino) carbonylmethoxy)phenylalanine-N-methylamide;
N-[4-Hydroxyamino-4-oxo-2R-isobutylbutanoy]-L-4-(methoxycarbonylmethoxy) phenylalanine-N-methylamide;
N-[4-Hydroxyamino-4-oxo-2R-isobutylbutanoy]-L-4-((N-benzylamino) carbonylmethoxy)phenylalanine-N-methylamide;
N-[4-Hydroxyamino-4-oxo-2R-isobutylbutanoy]-L-4-(ethoxycarbonylmethoxy) phenylalanine-N-methylamide;
N-[4-Hydroxyamino-4-oxo-2R-isobutylbutanoy]-L-4-((N,N-dimethylamino) carbonylmethoxy)phenylalanine-N-methylamide;
N-[4-Hydroxyamino-4-oxo-2R-isobutylbutanoy]-L-4-(aminocarbonylmethoxy) phenylalanine-N-methylamide;
and salts thereof.

* * * * *